United States Patent [19]

Hayase et al.

[11] Patent Number: 4,663,314

[45] Date of Patent: May 5, 1987

[54] ETHER COMPOUNDS CARRYING SUBSTITUTED SILYL GROUP

[75] Inventors: Yoshio Hayase, Kameyama; Toshikazu Ohtsuka, Kouga; Takeo Ishiguro, Kusatsu; Toshio Takahashi, Nishinomiya, all of Japan

[73] Assignee: Shionogi & Co., Ltd., Osaka, Japan

[21] Appl. No.: 860,220

[22] Filed: May 6, 1986

[30] Foreign Application Priority Data

May 16, 1985 [JP] Japan .................. 60-105465

[51] Int. Cl.$^4$ ............ A61K 31/695; C07F 7/08
[52] U.S. Cl. ........................ 514/63; 546/14; 549/214; 556/427; 556/445
[58] Field of Search .............. 546/14; 549/214; 556/427, 445; 514/63

[56] References Cited

U.S. PATENT DOCUMENTS 2,150,601  3/1939  Flint .......................... 546/14

Primary Examiner—Robert T. Bond
Attorney, Agent, or Firm—Wenderoth, Lind & Ponack

[57] ABSTRACT

A compound of the formula:

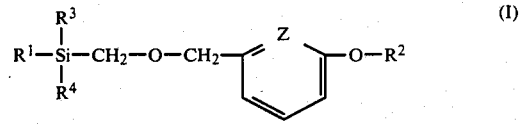

wherein $R^1$ and $R^2$ are each phenyl optionally substituted by one selected from the group consisting of $C_1$–$C_5$ alkyl, $C_1$–$C_5$ alkoxy, $C_1$–$C_5$ alkylthio, $C_1$–$C_5$ alkylenedioxy, halogen, nitro, and halogeno-$C_1$–$C_5$ alkoxy; $R^3$ and $R^4$ are each $C_1$–$C_5$ alkyl; and Z is N or CH. A method for preparing the compound (I) and a pesticidal formulation containing the same are also provided.

7 Claims, No Drawings

ETHER COMPOUNDS CARRYING SUBSTITUTED SILYL GROUP

This invention relates to novel ether compounds carrying a substituted silyl group which have been found to be particularly effective in the suppression of pests or undesirable species of insects, to their preparation, to their use and to pesticidal formulations containing the novel compounds.

Japanese Patent Publication (not examined) No. 196803/1984, No. 227861/1984, No. 72928/1982 & 154427/1981, and No. 72928/1982, close references found, respectively disclose 2,2-dimethyl-phenylethyl benzyl ethers, 2,2-dimethyl(or diethyl)-2-arylethyl phenoxypyridylmethyl(or pyridyloxybenzyl) ethers, 2-methyl-2-methyl(or ethyl)-2-arylethyl phenoxybenzyl ethers, and 2-methyl-2-methyl(or ethyl)-2-arylethyl benzylfurfuryl(or phenylthiobenzyl, benzoylbenzyl or benzylbenzyl) ethers which have pesticidal activity.

The ether compounds of the present invention are those having a substituted silyl group, and are therefore quite different from the compounds disclosed in the above references.

According to the present invention there is provided an ether compound having a substituted silyl group represented by the formula (I):

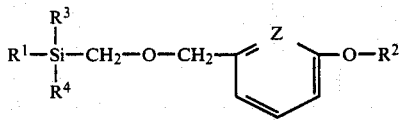
(I)

wherein $R^1$ and $R^2$ are each phenyl optionally substituted by one selected from the group consisting of $C_1-C_5$ alkyl, $C_1-C_5$ alkoxy, $C_1-C_5$ alkylthio, $C_1-C_5$ alkylenedioxy, halogen, nitro, and halogeno-$C_1-C_5$ alkoxy; $R^3$ and $R^4$ are each $C_1-C_5$ alkyl; and Z is N or CH.

The compound of the invention has an excellent pesticidal activity and no undesirable action to the higher animals, such as fish. Accordingly, the invention also provides a pesticidal formulation which comprises as an active ingredient from 0.1 to 95% by weight of a compound of the formula (I) associated with at least one carrier or diluent therefor.

This invention also provides a method of suppressing undesirable species of insects or pests which comprises applying to the locus of the pests a compound of the formula (I).

This invention further provides a process for preparing a compound of the formula (I) which comprises either (A) reacting a compound of the formula:

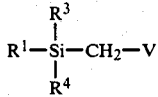
(II)

with a compound of the formula:

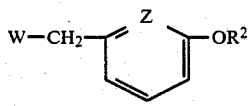
(III)

or (B) reacting a compound of the formula:

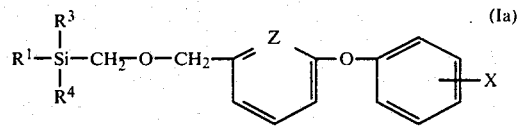
(Ia)

with a compound of the formula:

$$Y-R^5 \quad (IV)$$

wherein $R^5$ is $C_1-C_5$ alkyl; one of V and W is hydroxyl or its metal salt and the other is halogen or reactive ester of hydroxyl; X is metal or halogen; Y is halogen or reactive ester of hydroxy; $R^1$, $R^2$ $R^3$ $R^4$ and Z are as defined above.

The compound of the formula (I) has a chiral center and, therefore, can exist as either one of two possible stereoisomers or a mixture thereof. The invention includes such isomers and mixture thereof.

The term "$C_1-C_5$ alkyl" herein employed refers to a straight or branched saturated aliphatic hydrocarbon radical such as methyl, ethyl, propyl, isopropyl, butyl, isobutyl, sec-butyl, tert-butyl, pentyl, isopentyl, neopentyl, tert.-pentyl, or 1-methylisobutyl. Among them methyl and ethyl are preferred.

"$C_1-C_5$ alkoxy" refers to an alkoxy group containing $C_1-C_5$ alkyl moiety defined above and includes methoxy, ethoxy, propoxy, isopropoxy, butoxy, and pentoxy. "$C_1-C_5$ alkylthio" refers to an alkylthio group containing $C_1-C_5$ alkyl moiety defined above and includes methylthio, ethylthio, propylthio, isopropylthio, butylthio, and pentylthio.

"$C_1-C_5$ alkylenedioxy" refers to an alkylenedioxy group containing one to five carbon atoms, such as methylenedioxy, ethylenedioxy, or propylenedioxy.

The term "halogen" or "halogeno" refers to fluorine, chlorine, bromine, and iodine.

The term "halogeno-$C_1-C_5$ alkoxy" designates an afore-mentioned $C_1-C_5$ alkoxy arbitrarily substituted by one or more of halogen atoms, preferably not more than three halogen atoms, such as chloromethoxy, bromomethoxy difluoromethoxy, trifluoromethoxy, 1,2-dichloroethoxy, or 1,2,2-trichloroethoxy.

A metal salt of a hydroxyl group as used in the process for preparing the compound (I) of the invention may be an alkali metal salt such as sodium or potassium salt, an alkaline earth metal salt such as calcium or barium salt, or a silver salt. A reactive ester of a hydroxyl group includes an inorganic acid ester such as sulfate, or phosphate and an organic acid ester such as methanesulfonate, toluenesulfonate, trifluoromethanesulfonate and oxalate. THe symbol "X" refers to an alkali metal such as sodium or potassium, or an alkaline earth metal such as calcium or balium.

The process for preparing the compound (I) is detailed below.

METHOD A

The compound (I) of the invention is prepared by condensation of the compound (II) and the compound (III) described hereinbefore. Where either of V in compound (II) and W in compound (III) is hydroxy, the condensation is generally conducted in the presence of a base. As the base employed in the reaction, there may be exemplified organic bases, for example, alkali or alkaline earth metal hydroxides such as sodium hydroxide, potassium hydroxide and barium hydroxide; alkali or alkaline earth metal hydrides such as sodium hydride; alkali or alkaline earth metal amides such as sodium amide; alkali carbonates such as sodium carbonate and postassium carbonate; metal oxides such as barium oxide and silver oxide; and organic bases, for example, trialkyl amines such as triethylamine; and basic heterocyclic compounds such as 2,6-dimethylpyridine. It is often desirable to conduct the reaction in the presence of a catalyst selected from tetra-n-butylammonium bromide, copper iodide and copper dust.

The reaction is usually conducted in a solvent such as water or an organic solvent. The former is employed where sodium hydroxide or carbonate is used as a base and the latter is employed where the base is sodium hydride. Illustrative of the organic solvents are tetrahydrofuran, ether, dioxane, acetonitrile, dimethylformamide, dimethylsulfoxide, benzene and toluene.

The reaction temperature is not critical. However, preferable temperature is between 0° C. and around the boiling point of the solvent employed. The most preferred is from about room temperature to about 80° C.

The starting compound (II) wherein V is halogen may be prepared by the process disclosed in Japanese Patent Publicaton No. 4791/1983. The compound (II) wherein V is other than halogen may be derived from the compound (II) wherein V is halogen by processes well known to those skilled in the art. For instance, the compound (II) wherein V is hydroxyl is obtained by reacting a corresponding halogeno compound (II) with potassium acetate, and subsequently treating the resulting product with lithium aluminum hydride.

The staring compounds (III) are known or prepared by processes which are known or analogous to known processes.

METHOD B

The compound (Ib) of the present invention is prepared by the reaction of the compound (Ia) with the compound (IV).

The reaction is generally carried out in the presence of a strong base where X in compound (Ia) is halogen. As the strong base, an alkali metal such as sodium metal or an alkyl alakli metal such as butyl lithium is employed.

The reaction is generally carried out in the presence of a solvent such as tetrahydrofuran or ethyl ether. Preferable reaction temperature ranges from about −80° C. to around room temperature.

The starting compound (Ia) is prepared by the aforementioned method A.

The compound of the invention are useful for the control of pests of cultivated plants as well as medical or sanitary pests. Such pests include those of Order Lepidoptera (e.g. Spodoptera, Plutella, Adoxophyes, Dendrolinus, etc.), Hemiptera (e.g. Nephotettix, Myzus, Aphis, etc.), Coleoptera (e.g. Periplaneta, Cannosobruchus) and Acarina. Accordingly, a further embodiment of this invention is a method of controlling such undesirable insects or pests using the compound of the invention. In addition, the invention also provides a pesticidal formulation containing the compound of the invention.

The pesticidal formulations provided by the invention can take the form of emulsifiable concentrates, wettable powders, dusts, granules, oil solutions and dispersions, fumigations, smokes (e.g. buring or electro-heated mosquito-repellent incense), non-heated smokes, poisoning baits, aerosol preparations and the like. The formulations are generally produced by mixing between 0.1 and 95% by weight of the compound of the invention with one or more of suitable solid, liquid or gaseous carrier or adjuvants such as surfactant, dispersing agent, stabilizing agent, wetting agent and spreading agent, etc.

As solid carriers there may be exemplified clays (e.g. kaolin, bentonite, montmorillonite, pyrophyllite, sericite, etc.), talks, and other inorganic minerals (e.g. hydrated silicon dioxide, pumice, diatomaceous earth, sulfur dust, activated carbon, etc.).

Examples of liquid carriers are alcohols (e.g. methyl alcohol), ketons (e.g. acetone, methyl ethyl keton), ethers (ethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene), esters, nitrils, acid amides (e.g. dimethylformamide, dimethylacetamide), halogenated hydrocarbons (e.g. dichloroethane, trichloroethylene, carbon tetrachloride).

Surfactants employed in the formulations are preferably chosen from among alkyl sulfates, alkylsulfonates alkylarylsulfonates, polyethyleneglycol ether, and polyalcohol esters.

Illustrative of adhesive and dispersing agents are casein, gelatin, starch, CMC, acacia, alginic acid, lignin sulfonate, bentonite, molasses, polyvinyl alcohol, pine root oil, and agar. Typical stabilizers are PAP (isopropyl phosphate), TCP (tricresyl phosphate), tall oil, epoxidated oil, various surfactants and various fatty acids and esters thereof.

As is well understood, the formulations containing an active compound of this invention may also include one or more of other pesticidal compounds as well as antibiotics, herbicides, soil-improving agents and fertilizers.

The amount of the present active compound applied to the locus of pests will vary with a number of factors, including the way, time, and locus of application, the nature of pest(s) to be controlled, and the crops to be protected from such pests. In general, however, good results can be achieved at the application rate of 1–500 g/10 are.

The formulation of the invention can be applied to paddy field, corn and vegetable field, orchard, mulberry field, lawn, meadow, forest, flower garden, housing land and the like.

The following detailed Examples, Preparations and Experiments are presented by way of illustration of certain specific embodiments of the invention, wherein the following abbreviations are employed.

TBAB: tetra-n-butylammonum bromide
THF: tetrahydrofuran
DMSO: dimethyl sulfoxide

EXAMPLE 1

Dimethylphenylsilylmethyl 3-phenoxybenzyl ether (Method A)

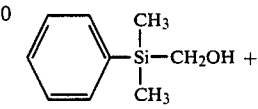

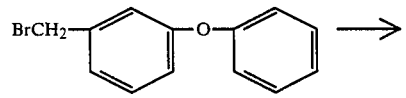

-continued

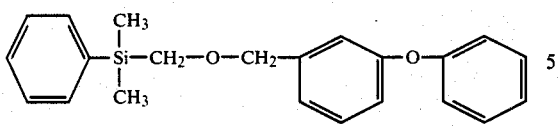

(Compound No. 1)

A mixture of dimethylphenylsilylmethanol (0.33 gram), 50% aqueous sodium hydroxide solution (1.20 gram), 3-phenoxybenzyl bromide (0.44 gram), and TBAB (0.07 gram) was stirred for 15 hours at room temperature. The reaction mixture was added with water and extracted with ethyl ether. The ether layer was washed with saturated sodium chloride solution, dried, and evaporated under vacuum to remove the solvent. The residue was purified by column chromatography over silica gel (20 gram) using as the eluent n-hexane:ethyl acetate (100:1), to obtain the title compound. Yield 0.32 gram. Physicochemical properties of the product are listed in Table 2.

EXAMPLE 2-42

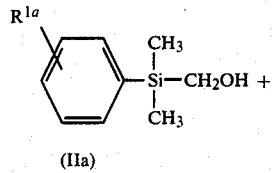

(IIa)

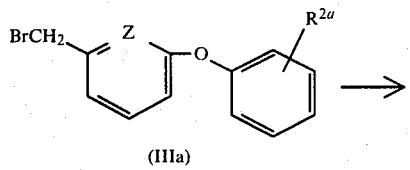

(IIIa)

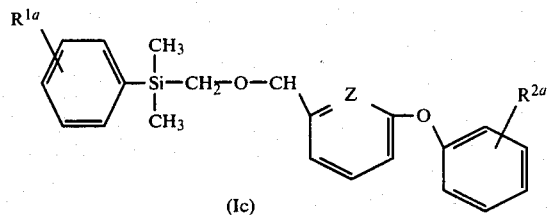

(Ic)

A mixture of the compound of the formula (IIa), 50% sodium hydroxide solution, the compound of the formula (IIIa) and TBTB are allowed to react with stirring. Following addition of water to the reaction mixture, ethyl ether extraction was conducted. The ether extract was washed with saturated sodium chloride solution, and the solvent was removed by evaporation under vacuum. The resulting crude residue was purified by column chromatography to obtain the ultimate product (Ic).

Table 1 lists specific products produced by the general method mentioned above, wherein there are provided the identity of $R^{1a}$ in compound (IIa), and $R^{2a}$ and Z in compound (IIIa); respective amounts of compounds (IIa) and (IIIa), 50% sodium hydroxide, and TBAB employed in the reaction; reaction conditions; chromatographic conditions; yield of product (Ic) based on the starting compound (IIa). Physiocochemical properties of the product (Ic), however, are shown in Table 2.

TABLE 1

| Example No. | Compound No. | $R^{1a}$ | $R^{2a}$ | Z | Compound IIa (g) | Compound IIIa (g) | 50%-NaOH (g) | TBAB (g) | Reaction Temp. (°C.) | Reaction Time (hr) | Chromatograph silica gel (g) | n-Hexane: Ethyl acetate | Yield (%) |
|---|---|---|---|---|---|---|---|---|---|---|---|---|---|
| 1 | 1 | H | H | CH | 0.33 | 0.44 | 1.20 | 0.07 | RT | 15 | 20 | 100:1 | 46 |
| 2 | 2 | H | 4-Cl | CH | 0.17 | 0.25 | 0.75 | 0.04 | 80 | 1 | 12 | 100:1 | 49 |
| 3 | 3 | H | 2-Cl | CH | 0.19 | 0.29 | 0.85 | 0.05 | 80 | 1 | 14 | 100:1 | 46 |
| 4 | 4 | H | 3-Cl | CH | 0.26 | 0.37 | 1.02 | 0.08 | 80 | 1 | 20 | 100:1 | 55 |
| 5 | 5 | H | 4-Br | CH | 0.18 | 0.31 | 0.80 | 0.05 | 80 | 1 | 15 | 100:1 | 50 |
| 6 | 7 | 4-Cl | H | CH | 0.30 | 0.35 | 1.20 | 0.09 | RT | 24 | 20 | 100:1 | 56 |
| 7 | 8 | 4-$C_2H_5O$ | 4-F | CH | 0.33 | 0.44 | 1.26 | 0.10 | RT | 24 | 22 | 100:1.2 | 68 |
| 8 | 9 | 4-Cl | 3-Cl | CH | 0.40 | 0.52 | 1.00 | 0.13 | RT | 24 | 30 | 100:1 | 59 |
| 9 | 10 | 4-$C_2H_5O$ | 3-Cl | CH | 0.32 | 0.43 | 1.20 | 0.09 | RT | 23 | 21 | 100:1:2 | 74 |
| 10 | 11 | 4-$C_2H_5O$ | 4-$NO_2$ | CH | 0.32 | 0.43 | 1.20 | 0.10 | RT | 24 | 21 | 100:4 | 71 |
| 11 | 12 | H | 4-F | CH | 0.25 | 0.38 | 1.20 | 0.10 | RT | 23 | 20 | 100:1 | 64 |
| 12 | 13 | H | 4-$NO_2$ | CH | 0.25 | 0.40 | 1.20 | 0.10 | RT | 20 | 18 | 100:3 | 59 |
| 13 | 14 | 4-$C_2H_5O$ | 2-Cl | CH | 0.35 | 0.45 | 0.60 | 0.11 | RT | 24 | 25 | 100:1.2 | 68 |
| 14 | 15 | 4-F | H | CH | 0.31 | 0.40 | 0.67 | 0.11 | RT | 24 | 22 | 100:1 | 55 |
| 15 | 16 | 4-$CH_3O$ | 4-F | CH | 0.33 | 0.42 | 0.67 | 0.11 | RT | 24 | 24 | 100:1.2 | 33 |
| 16 | 17 | 4-Cl | 4-F | CH | 0.41 | 0.52 | 0.80 | 0.14 | RT | 23 | 30 | 100:1 | 68 |
| 17 | 18 | 4-$C_2H_5O$ | 4-Cl | CH | 0.40 | 0.51 | 0.76 | 0.13 | RT | 24 | 28 | 100:1.2 | 58 |
| 18 | 19 | 4-$CH_3O$ | H | CH | 1.01 | 1.18 | 3.20 | 0.32 | RT | 20 | 65 | 100:1.2 | 46 |
| 19 | 20 | H | 4-$CH_3O$ | CH | 0.28 | 0.47 | 1.27 | 0.11 | RT | 24 | 23 | 100:1.2 | 63 |
| 20 | 21 | 4-$C_2H_5O$ | 4-$CH_3O$ | CH | 0.33 | 0.45 | 1.18 | 0.10 | RT | 24 | 24 | 100:1.8 | 52 |
| 21 | 23 | 4-Cl | 4-$CH_3O$ | CH | 0.22 | 0.32 | 0.65 | 0.07 | RT | 20 | 15 | 100:1.2 | 54 |
| 22 | 24 | 4-$CH_3O$ | 4-$CH_3O$ | CH | 0.22 | 0.32 | 0.65 | 0.07 | RT | 21 | 15 | 100:1.8 | 50 |
| 23 | 25 | 4-$CH_3$ | H | CH | 0.36 | 0.52 | 1.20 | 0.13 | RT | 20 | 27 | 100:1 | 87 |
| 24 | 26 | 3-$CH_3$ | H | CH | 0.38 | 0.51 | 1.20 | 0.13 | RT | 24 | 27 | 100:1 | 65 |
| 25 | 27 | 4-$C_2H_5O$ | H | N | 0.29 | 0.33 | 1.00 | 0.09 | RT | 16.5 | 18 | 100:4 | 55 |
| 26 | 28 | H | H | N | 0.17 | 0.26 | 0.80 | 0.07 | RT | 14 | 13 | 100:3 | 59 |
| 27 | 29 | 4-Cl | H | N | 0.16 | 0.19 | 0.64 | 0.05 | RT | 16 | 11 | 100:3 | 56 |
| 28 | 30 | 4-$CH_3$ | H | N | 0.12 | 0.17 | 0.50 | 0.04 | RT | 24 | 10 | 100:3 | 60 |
| 29 | 31 | 4-$CH_3O$ | H | N | 0.14 | 0.16 | 0.80 | 0.04 | RT | 20 | 10 | 100:4 | 52 |
| 30 | 32 | 4-F | H | N | 0.18 | 0.25 | 0.80 | 0.06 | RT | 12 | 14 | 100:3 | 55 |
| 31 | 33 | 3-Cl | H | CH | 0.40 | 0.52 | 1.20 | 0.13 | RT | 20 | 30 | 100:1 | 65 |

TABLE 1-continued

| Example No. | Compound No. | $R^{1a}$ | $R^{2a}$ | Z | Compound IIa (g) | Compound IIIa (g) | 50%-NaOH (g) | TBAB (g) | Reaction Temp. (°C.) | Reaction Time (hr) | Chromatograph silica gel (g) | n-Hexane: Ethyl acetate | Yield (%) |
|---|---|---|---|---|---|---|---|---|---|---|---|---|---|
| 32 | 34 | 3-CH$_3$O | H | CH | 0.50 | 0.60 | 2.00 | 0.16 | RT | 24 | 35 | 100:1.2 | 64 |
| 33 | 35 | 2-C$_2$H$_5$ | H | CH | 0.20 | 0.24 | 0.82 | 0.07 | RT | 24 | 15 | 100:1 | 60 |
| 34 | 36 | 2-C$_2$H$_5$O | H | CH | 0.70 | 0.79 | 2.60 | 0.22 | RT | 24 | 45 | 100:1.2 | 70 |
| 35 | 37 | 3-C$_2$H$_5$O | H | CH | 0.30 | 0.34 | 1.14 | 0.09 | RT | 24 | 20 | 100:1.2 | 62 |
| 36 | 38 | 4-C$_2$H$_5$S | H | CH | 0.50 | 0.52 | 1.77 | 0.14 | RT | 24 | 30 | 100:1.2 | 58 |
| 37 | 39 | 3,4-OCH$_2$O | H | CH | 0.50 | 0.56 | 1.80 | 0.15 | RT | 24 | 33 | 100:1.8 | 64 |
| 38 | 40 | 4-(CH$_3$)$_2$CHO | H | CH | 0.30 | 0.32 | 1.10 | 0.09 | RT | 24 | 20 | 100:1.2 | 55 |
| 39 | 41 | 4-CHF$_2$O | H | CH | 0.30 | 0.31 | 1.03 | 0.08 | RT | 24 | 20 | 100:1.2 | 58 |
| 40 | 42 | 3,4-OCH$_2$O | H | N | 0.25 | 0.28 | 0.95 | 0.08 | RT | 20 | 15 | 100:5 | 62 |
| 41 | 43 | 4-CHF$_2$O | H | N | 0.25 | 0.26 | 0.86 | 0.07 | RT | 20 | 15 | 100:4 | 60 |
| 42 | 44 | 4-(CH$_3$)$_2$CHO | H | N | 0.25 | 0.27 | 0.89 | 0.07 | RT | 20 | 15 | 100:4 | 56 |

EXAMPLE 43

Dimethyl(4-ethoxyphenyl)silylmethyl 3-phenoxybenzyl ether (Method A)

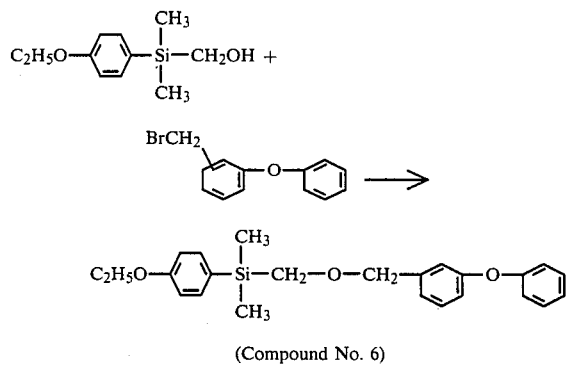

(Compound No. 6)

A mixture of dimethyl(4-ethoxyphenyl)silylmethanol (0.22 gram), 3-phenoxybenzyl bromide (0.24 gram), TBAB (0.07 gram), potassium carbonate (0.40 gram) and water (1.0 gram) was stirred 15 hours at 80° C. After cooling, the reaction mixture was extracted with ethyl ether, and the extract was washed with saturated sodium chloride solution, dried, and evaporated under vacuum to remove the solvent. The residue was purified by column chromatography over silica gel (13 gram) using n-hexane:ethyl acetate (100:1.2) as the eluent to obtain the title compound. Yield 0.23 gram. Physicochemical properties of the product are listed in Table 2.

EXAMPLE 44

Dimethyl(4-ethoxyphenyl)silylmethyl 3-phenoxybenzyl ether (Method A)

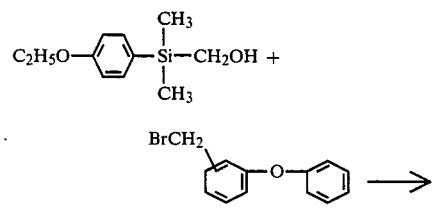

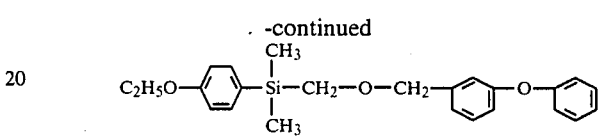

(Compound No. 6)

Dimethyl(4-ethoxyphenyl)silylmethanol (0.25 gram), 50% sodium hydride (0.17 gram), and 3-phenoxybenzyl bromide (0.2 gram) were dissolved in 3 ml of THF and the resulting mixture was stirred for 2.5 hours at 80° C. After cooling, the mixture was added with ice, diluted with ethyl ether, and washed with saturated sodium chloride solution. The ether layer was dried and evaporated under vacuum to remove the solvent.

The residue was purified by column chromatography over silica gel (15 gram) using n-hexane:ethyl acetate (100:1.2) as the eluent to obtain the title compound. Yield 0.32 gram. Physicochemical properties of the product are listed in Table 2.

EXAMPLE 45

Dimethylphenylsilylmethyl 3-(4-methylphenoxy)benzyl ether (Method B)

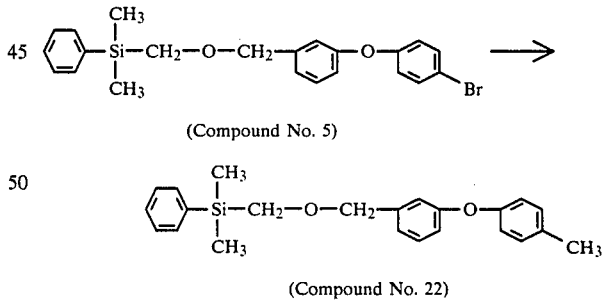

(Compound No. 22)

Dimethylphenylsilylmethyl 3-(4-bromophenoxy)benzyl ether (0.53 gram) was dissolved in 3 ml of THF. To the mixture were added 1.0 ml of 1.55M n-butyl lithium and subsequently 1 ml of methyl iodide with stirring at −78° C. and the stirring was continued for 10 minutes at the same temperature and for 15 minutes at room temperature. After addition of water, the mixture was extracted with ethyl ether. The ether layer was washed with saturated sodium chloride solution, dried and evaporated under vacuum to remove the solvent. The residue was purified by column chromatography over silica gel (15 gram) using n-hexane:ethyl acetate (100:1) to obtain the title compound. Yield 0.42 gram. Physicochemical properties of the product are listed in Table 2.

TABLE 2

| Compound No. | $n_D$ (Temp.) | IR(liquid) (cm$^{-1}$) | NMR (CDCl$_3$) (δ,ppm) | Mass Spectrum (B:Base Peak) | Molecular Formula Elemental Analysis Calculated Found C / H / N |
|---|---|---|---|---|---|
| 1 | 1.5686 (25.6) | 3055,2945,2830, 2790,1580,1480, 1245,1210,835, 685 | 0.31(6H,s)3.28(2H, s,),4.39(2H,s), 6.68–7.63(14H,m) | 348(M$^+$),333, 165,135(B) | C$_{22}$H$_{24}$O$_2$Si<br>74.82  6.94  —<br>76.01  6.97  — |
| 2 | 1.5743 (26.0) | 3060,2950,2840, 2795,1575,1480, 1250,815,720, 690 | 0.31(6H,s),3.29(2H, s,),4.41(2H,s), 6.84–7.60(13H,m) | 382(M$^+$),367, 165,135(B) | C$_{22}$H$_{23}$O$_2$ClSi<br>69.00  6.05  —<br>67.15  5.77  — |
| 3 | 1.5751 (25.0) | 3060,2950,2835, 2795,1575,1470, 1445,1260,1250, 835,690 | 0.31(6H,s),3.32(2H, s),4.45(2H,s), 6.70–7.70(13H,m) |  | C$_{22}$H$_{23}$O$_2$ClSi<br>69.00  6.05  —<br>69.09  6.22  — |
| 4 | 1.5783 (25.5) | 8070,2960,2850, 2810,1585,1475, 1255,845,705 | 0.32(6H,s),3.33(2H, s),4.47(2H,s), 6.62–7.67(13H,m) |  | C$_{22}$H$_{23}$O$_2$ClSi<br>69.00  6.05  —<br>65.68  5.67  — |
| 5 | 1.5861 (24.6) | 3055,2945,2830, 2790,1570,1480, 1250,1070,835, 690 | 0.32(6H,s),3.34(2H, s),4.47(2H,s), 6.76–7.75(13H,m) |  | C$_{22}$H$_{23}$O$_2$BrSi<br>61.82  5.42  —<br>60.98  5.44  — |
| 6 | 1.5648 (25.6) | 3020,2975,2845, 2800,1595,1485, 1250,1115,840, 690 | 0.28(6H,s),1.36(3H, t,J=7Hz),3.25(2H,s), 3.96(2H,q,J=7Hz), 4.39(2H,s),6.65–7.46 (13H,m) | 392(M$^+$),377 179(B) | C$_{24}$H$_{28}$O$_3$Si<br>73.43  7.19  —<br>73.42  7.21  — |
| 7 | 1.5728 (25.5) | 2950,2840,2790, 1580,1485,1250, 1085,840,690 | 0.28(6H,s),3.28(2H, s),4.42(2H,s), 6.73–7.54(13H,m) | 382(M$^+$),169(B) | C$_{22}$H$_{23}$O$_2$ClSi<br>69.00  6.05  —<br>69.22  6.14  — |
| 8 | 1.5551 (26.2) | 2970,2835,2795, 1590,1495,1250, 1200,1115,840, 690 | 0.29(6H,s),1.39(3H, t,J=7Hz),3.29(2H,s), 4.02(2H,q,J=7Hz), 4.44(2H,s),6.71–7.55 (12H,m) | 410(M$^+$),395, 179(B),135 | C$_{24}$H$_{27}$O$_3$FSi<br>70.21  6.63  —<br>70.26  6.61  — |
| 9 | 1.5890 (25.7) | 3050,2945,2830, 2790,1575,1480, 1465,1250,1080, 835,800,690 | 0.30(6H,s),3.30(2H, s),4.45(2H,s), 6.73–7.63(12H,m) | 401,169(B) | C$_{22}$H$_{22}$O$_2$Cl$_2$Si<br>63.31  5.31  —<br>62.99  5.67  — |
| 10 | 1.5702 (25.8) | 3020,2975,2845, 2800,1595,1580, 1470,1245,1115, 840,695,675 | 0.29(6H,s),1.37(3H, t,J=7Hz),3.28(2H,s), 3.98(2H,q,J=7Hz), 4.42(2H,s),6.67–7.50 (12H,m) |  | C$_{24}$H$_{27}$O$_3$ClSi<br>67.51  6.37  —<br>67.99  6.53  — |
| 11 | 1.5828 (25.8) | 2975,2845,2800, 1590,1580,1515, 1485,1340,1250, 1115,850,750, 685,700 | 0.31(6H,s)1.37(3H, t,J=7Hz),3.30(2H,s), 3.95(2H,q,J=7Hz), 4.45(2H,s),6.69–8.13 (12H,m) | 407,179(B) | C$_{24}$H$_{27}$O$_5$NSi<br>65.88  6.22  3.20<br>66.12  6.04  3.37 |
| 12 | 1.5632 (25.6) | 3065,2955,2845, 2795,1585,1500, 1485,1260,1205, 845,700 | 0.31(6H,s)3.28(2H, s),4.38(2H,s), 6.43–7.58(13H,m) | 366(M$^+$),351, 165(B),135 | C$_{22}$H$_{23}$O$_2$FSi<br>72.10  6.33  —<br>70.55  6.45  — |
| 13 | 1.5900 | 3065,2950,2845 2800,1575,1510, 1485,1345,1245, 1110,840,750, 730,695 | 0.33(6H,s),3.35(2H s),4.48(2H,a), 6.80–8.27(13H,m) |  | C$_{22}$H$_{23}$NO$_4$Si<br>67.15  5.89  3.56<br>66.89  6.10  3.65 |
| 14 | 1.5703 (25.7) | 2965,2840,1590 1575,1470,1250, 1110,840,680 | 0.27(6H,s),1.36(3H, t,J=7Hz),3.23(2H,s), 3.95,(2H,q,J=7Hz), 4.38(2H,s),6.66–7.41 (12H,m) |  | C$_{24}$H$_{27}$O$_3$ClSi<br>67.51  6.37  —<br>67.76  6.39  — |
| 15 | 1.5594 (25.6) | 3030,2955,2845, 2800,1585,1490, 1255,1165,1110, 850,825,695 | 0.30(6H,s),3.28(2H, s),4.42(2H,s), 6.72–7.62(13H,m) | 366(M$^{+1}$),351, 183(B) | C$_{22}$H$_{23}$O$_2$FSi<br>72.10  6.33  —<br>72.29  6.43  — |
| 16 | 1.5657 (25.7) | 3060,3010,2950, 2840,2795,1590, 1495,1485,1445 1250,1200,1115, 840,780,690 | 0.28(6H,s),3.26(2H, s),3.73(3H,s),4.38 (2H,s),6.59–7.49 (12H,m) | 381,165(B) | C$_{23}$H$_{25}$O$_3$FSi<br>69.67  6.36  —<br>69.80  6.53  — |
| 17 | 1.5675 (25.8) | 3050,2945,2830 2785,1580,1490 1480,1250,1195, 1080,830,800, 775,690 | 0.30(6H,s),3.27(2H, s),4.41(2H,s), 6.57–7.54(12H,m) | 400(M$^+$),385, 199,169(B) | C$_{22}$H$_{22}$O$_2$FClSi<br>65.90  5.53  —<br>65.96  5.67  — |
| 18 | 1.5702 | 2975,2840,2800, | 0.28(6H,s),1.37(3H, | 411(M$^+$),179(B) | C$_{24}$H$_{27}$O$_3$ClSi |

TABLE 2-continued

| Compound No. | n_D (Temp.) | IR(liquid) (cm$^{-1}$) | NMR (CDCl$_3$) (δ,ppm) | Mass Spectrum (B:Base Peak) | Molecular Formula Elemental Analysis Calculated Found | | |
|---|---|---|---|---|---|---|---|
| | | | | | C | H | N |
| | (25.8) | 1590,1485,1245, 830,690 | t,J=7(Hz),3.25(2H,s), 3.97(2H,q,J=7Hz) 4.39(2H,s),6.72-7.42 (12H,m) | | 67.51 67.09 | 6.37 6.61 | — — |
| 19 | 1.5696 (25.7) | 2955,2835,1590, 1490,1250,1115, 845,690 | 0.28(6H,s)3.24(2H, s),3.71(3H,s),4.38 (2H,s)6.67-7.50 (13H,m) | 378(M$^+$),363, 165(B) | C$_{23}$H$_{26}$O$_3$Si 72.88 73.37 | 6.92 7.03 | — — |
| 20 | 1.5746 (25.4) | 3070,3050,2960, 2845,2805,1610, 1590,1505,1240, 1210,840,700 | 0.31(6H,s),3.31(2H, s),3.76(3H,s),4.43 (2H,s),6.56-7.67 (13H,m) | 378(M$^+$),363, 135(B) | C$_{23}$H$_{26}$O$_3$Si 72.98 72.92 | 6.92 6.99 | — — |
| 21 | 1.5649 (25.5) | 2950,2825,2800, 1595,1500,1250, 1210,1115,1040, 840,690 | 0.28(6H,s)1.38(3H, t,J=7(Hz),3.28(2H,s), 3.78(3H,s)4.02(2H, q,J=7Hz),4.43(2H,s), 6.72-7.55(12H,m) | | C$_{25}$H$_{30}$O$_4$Si 71.05 70.97 | 7.16 7.20 | — — |
| 22 | 1.5682 (25.3) | 3065,3020,2955, 2850,2800,1590, 1505,1485,1250, 1220,840,730, 695 | 0.30(6H,s),2.28(3H, s),3.27(2H,s),4.39 (2H,s)6.66-7.63 (13H,m) | 362(M$^+$),347, 135(B) | C$_{23}$H$_{26}$O$_2$Si 76.20 76.82 | 7.23 7.38 | — — |
| 23 | 1.5643 (25.7) | 2940,2820,2790, 1580,1570,1495, 1480,1440,1235, 1205,1080,835, 800,685 | 0.28(6H,s),3.28(2H, s),3.78(3H,s),4.42 (2H,s)6.62-7.58 (12H,m) | | C$_{23}$H$_{25}$O$_3$ClSi 66.89 66.71 | 6.10 6.17 | — — |
| 24 | 1.5496 (25.4) | 2995,2950,2895, 2830,2800,1590, 1500,1240,1110, 1030,830,685 | 0.28(6H,s)3.25(2H, s),3.72(6H,s),4.38 (2H,s),6.63-7.53 (12H,m) | | C$_{24}$H$_{28}$O$_4$Si 70.55 70.72 | 6.91 6.95 | — — |
| 25 | 1.5620 (25.3) | 3060,3025,2950, 2840,2795,1585, 1485,1250,1215, 1110,840,795, 690 | 0.28(6H,s),2.28(3H, s),3.25(2H,s),4.38 (2H,s),6.65-7.45 (13H,m) | 362(M$^+$),347, 179(B),149 | C$_{23}$H$_{26}$O$_2$Si 76.20 76.18 | 7.23 7.31 | — — |
| 26 | 1.5658 (25.1) | 3025,2945,2835, 2795,1580,1485, 1250,1210,870, 830,690 | 0.31(6H,s),2.30(3H, s),3.29(2H,s),4.42 (2H,s),6.62-7.56 (13H,m) | | | | |
| 27 | 1.5625 (25.2) | 3025,2980,2850, 2810,1595,1450, 1255,1120,850, 695 | 0.34(6H,s),1.39(3H, t,J=7Hz),3.42(2H,s), 4.04(2H,q,J=7Hz), 4.52(2H,s),6.56-7.80 (12H,m) | 394(M + H)$^+$,378, 185(B) | | | |
| 28 | 1.5646 (25.8) | 3075,2970,2860, 2815,1595,1580, 1495,1450,1260, 1125,850,700 | 0.37(6H,s),3.45(2H, s),4.51(2H,s), 6.55-7.75(13H,m) | 334,185(B) | | | |
| 29 | 1.5729 (25.4) | 3060,2945,2835, 2790,1585,1570, 1485,1440,1250, 1080,840,800, 685 | 0.35(6H,s),3.42(2H, s),4.50(2H,s), 6.54-7.79(12H,m) | 383(M$^+$),367, 185(B) | C$_{21}$H$_{22}$NO$_2$ClSi 65.69 64.95 | 5.78 5.77 | 3.65 4.11 |
| 30 | 1.5634 (25.6) | 2950,2850,2800, 1595,1570,1450, 1255,1110,840, 795,690 | 0.34(6H,s),2.32(3H, s),3.38(2H,s),4.45 (2H,s),6.46-7.71 (12H,m) | | | | |
| 31 | 1.5674 (25.7) | 2945,2830,1585, 1570,1490,1445, 1250,1115,845, 690 | 0.34(6H,s),3.43(2H, s),3.82(3H,s),4.53 (2H,s),6.58-7.84 (12H,m) | | | | |
| 32 | 1.5579 (25.7) | 3055,3020,2950, 2840,2795,1585, 1570,1490,1440, 1250,1225,1160, 1150,840,685 | 0.34(6H,s),3.39(2H, s),4.47(2H,s), 6.50-7.72(12H,m) | | | | |
| 33 | 1.5349 (26.0) | 3030,2950,2830, 1580,1485,1250, 1210,840,780 | 0.30(6H,s),3.28(2H, s),4.42(2H,s), 6.71-7.64(13H,m) | 382(M$^+$),367, 199,183(B) | C$_{22}$H$_{23}$O$_2$ClSi 69.00 71.41 | 6.05 6.43 | — — |
| 34 | 1.5690 (26.0) | 3030,2940,2830, 1585,1485,1250, 870,835,780, 690 | 0.30(6H,s),3.33(2H, s),3.79(3H,s),4.47 (2H,s),6.73-7.57 (13H,m) | 378(M$^+$),363, 165(B),121 | C$_{23}$H$_{26}$O$_3$Si 72.98 72.92 | 6.92 6.94 | — — |
| 35 | 1.5689 (25.9) | 3030,2950,2830, 1575,1475,1440, 1245,1210,1070, 835,750,685 | 0.36(6H,s),1.20(3H, t,J=7Hz),2.73(2H,q, J=7Hz),3.39(2H,s), 4.49(2H,s),6.70-7.70 | 376(M)$^+$,361, 271,193,163(B) | C$_{24}$H$_{28}$O$_2$Si 76.55 76.45 | 7.49 7.45 | — — |

TABLE 2-continued

| Compound No. | $n_D$ (Temp.) | IR(liquid) (cm$^{-1}$) | NMR (CDCl$_3$) ($\delta$,ppm) | Mass Spectrum (B:Base Peak) | Molecular Formula Elemental Analysis Calculated Found | | |
|---|---|---|---|---|---|---|---|
| | | | | | C | H | N |
| 36 | 1.5621 (25.9) | 3040,2950,2850, 1580,1480,1430, 1235,1070,835, 750,685 | 0.32(6H,s),1.33(3H, t,J=7Hz),3.40(2H,s), 3.95(2H,q,J=7Hz), 4.45(2H,s),6.53-7.57 (13H,m) | 392(M)$^+$,179(B) | C$_{24}$H$_{28}$O$_3$Si 73.43 | 7.18 | — |
| 37 | 1.5623 (25.8) | 3020,2950,2835, 1580,1475,1245, 830,775,685 | 0.30(6H,s),1.37(3H, t,J=7Hz),3.31(2H,s), 4.01(2H,q,J=7Hz), 4.47(2H,s),6.73-7.53 (13H,m) | 392(M)$^+$,377, 196,135(B) | C$_{24}$H$_{28}$O$_3$Si 73.43 73.26 | 7.18 7.22 | — — |
| 38 | 1.5847 (26.1) | 3045,2950,2830, 2790,1580,1485, 1250,1210,1075, 840,800,685 | 0.28(6H,s),1.28(3H, t,J=7hz),2.89(2H,q, J=7Hz),3.26(2H,s), 4.39(2H,s),6.63-7.47 (13H,m) | 408(M)$^+$,393, 225,195(B) 151 | C$_{24}$H$_{28}$O$_2$Si 70.54 71.30 | 6.91 6.95 | — — |
| 39 | 1.5777 (26.1) | 3050,2955,2850, 1590,1485,1235, 1045,840,805, 690 | 0.27(6H,s),3.31(2H, s),4.50(2H,s),5.95 (2H,s),6.72-7.47 (12H,m) | 392(M$^+$),377, 179(B) | C$_{23}$H$_{24}$O$_4$Si 70.37 70.08 | 6.16 5.99 | — — |
| 40 | 1.5590 (26.0) | 2965,2840,1590, 1490,1250,1110, 950,840,690 | 0.28(6H,s),1.32(6H, d,J=7Hz),3.30(2H,s), 4.47(2H,s),4.56(1H, hept.,J=7Hz),6.76-7.61 (13H,m) | 406(M)$^+$,363, 193(B),149 | C$_{25}$H$_{30}$O$_3$Si 73.85 73.99 | 7.44 7.41 | — — |
| 41 | 1.5483 (26.1) | 3025,2950,2845, 1585,1490,1380, 1250,1215,1130, 1070,1045,840, 690 | 0.30(6H,s),3.30(2H, s),4.44(2H,s),6.45 1H,t,J=74(Hz), 6.75-7.72(13H,m) | 414(M$^+$),399, 201(B),183 | C$_{23}$H$_{24}$O$_3$F$_2$Si 66.64 68.06 | 5.84 6.13 | — — |
| 42 | 1.5762 (25.9) | 3030,2945,2855, 1590,1570,1485, 1440,1230,1110, 1035,835,800, 685 | 0.32(6H,s),3.42(2H, s),4.53(2H,s),5.95 (2H,s),6.59-7.86 (11H,m) | 394(M + H)$^+$, 378,185(B) | C$_{22}$H$_{23}$NO$_4$Si 67.15 67.16 | 5.89 5.96 | 3.56 4.26 |
| 43 | 1.5439 (26.1) | 3015,2950,2840, 1590,1570,1490, 1440,1250,1220, 1125,1040,835, 800,690 | 0.35(6H,s),3.43(2H, s),4.52(2H,s),6.53 (1H,t,J=74Hz), 6.57-7.81(12H,m) | 416(M + H)$^+$, 400,185(B) | C$_{22}$H$_{23}$NO$_3$F$_2$Si 63.59 63.67 | 5.58 5.93 | 3.37 3.75 |
| 44 | 1.5549 (26.2) | 2965,2845,1590, 1495,1440,1270, 1245,1110,950, 840,690 | 0.34(6H,s),1.34(6H, d,J=7Hz),3.42(2H,s), 4.52(2H,s),4.58(1H, hept.,J=7Hz), 6.56-7.82(12H,m) | 408(M + H)$^+$, 392,272,185 (B) | C$_{24}$H$_{29}$NO$_3$Si 70.72 | 7.17 | 3.44 |

PREPARATION 1

Chloromethyldimethyl(4-ethoxyphenyl)silane

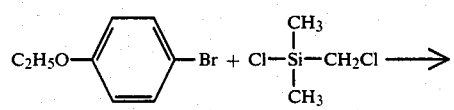

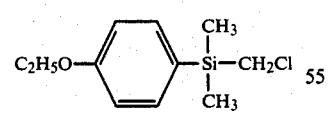

A mixture of 60 ml of THF, p-bromophenetole (9.7 gram) and chloromethyldimethylsilyl chloride (7.3 gram) was cooled in a dry ice/acetone bath. To the mixture was dropwise added 33 ml of 1.55M n-butyl lithium under an argon atmosphere. After stirring the mixture for additional 15 minutes at −78° C., the stirring was continued at room temperature for 30 minutes. The mixture was added with 6 ml of ethyl acetate and 30 ml of water, and extracted with ethyl ether. The ether extract was washed with saturated sodium chloride solution, dried, and concentrated. Distillation of the residue gave 5.5 gram of chloromethyldimethyl(4-ethoxyphenyl)silane. Physicochemical data of the product is listed in Table 3.

PREPARATION 2

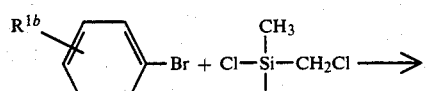

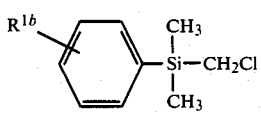

In the same manner as described in Preparation 1, various starting compounds listed in Table 3 were prepared according to the above synthetic schema.

PREPARATION 3

Dimethyl(4-ethoxyphenyl)silylmethanol

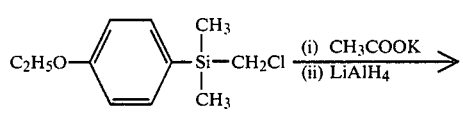

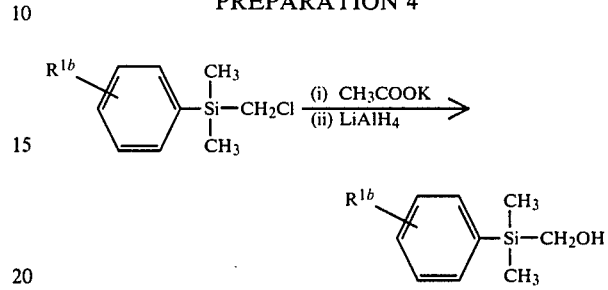

A mixture of chloromethyldimethyl(4-ethoxyphenyl)silane (0.55 gram), potassium acetate (0.47 gram) and 3 ml of DMSO was stirred for 1.5 hours at 90° C. After cooling to room temperature, the reaction mixture was added with water and extracted with ethyl ether. The ether extract was washed with saturated sodium chloride solution, dried, and concentrated. The residue (0.55 gram) was dissolved in 5 ml of ethyl ether. Lithium aluminum hydride (100 mg) was added to the resulting solution at 0° C. with stirring and the solution was stirred for 2 hours at the same temperature. After addition of a minimun amount of saturated ammonium chloride solution, the mixture was dried over anhydrous sodium sulfate, and concentrated. The residue was purified by column chromatography over silica gel (15 gram) using n-hexane:ethyl acetate (100:30) as the eluent to give the title compound as a white crystal. Yield 0.50 gram. Physicochemical data of the product is given in Table 4.

PREPARATION 4

In the same manner as described in Preparation 3, other starting compounds listed in Table 4 were obtained.

TABLE 3

| $R^{1b}$ | bp°C. (mmHg) | NMR (CDCl$_3$,δ,ppm) | Molecular Formula Elementary Analysis Calculated Found | | | |
|---|---|---|---|---|---|---|
| | | | C | H | Cl | F |
| 4-C$_2$H$_5$O | 103 (2) | 0.38(6H,s),1.40 (3H,J=7Hz),2.86 (2H,s),3.97(2H, q,J=7Hz),6.79 (2H,d,J=8Hz),7.34 (2H,d,J=8Hz) | C$_{11}$H$_{17}$ClOSi | | | |
| | | | 57.75 | 7.49 | 15.50 | — |
| | | | 57.76 | 7.59 | 15.53 | — |
| 4-CHF$_2$O | 80-82 (1) | 0.43(6H,s),2.90 (2H,s),6.45((1H, t,J=74Hz),7.05 2H,d,J=8Hz),7.48 (2H,d,J=8Hz) | C$_{10}$H$_{13}$ClF$_2$OSi | | | |
| | | | 47.90 | 5.23 | 14.14 | 15.15 |
| | | | 47.65 | 5.17 | 14.59 | 15.06 |
| 4-Cl | 93 (2) | | C$_9$H$_{12}$Cl$_2$Si | | | |
| | | | 49.32 | 5.52 | 32.35 | — |
| | | | 49.56 | 5.62 | 32.59 | — |
| 4-F | 62-63 (1) | | C$_9$H$_{12}$ClFSi | | | |
| | | | 53.32 | 5.97 | 17.49 | 9.37 |
| | | | 53.79 | 6.59 | 17.86 | 9.51 |
| 4-CH$_3$O | | | C$_{10}$H$_{15}$ClOSi | | | |
| | | | 55.93 | 7.04 | 16.51 | — |
| | | | 55.07 | 6.82 | 17.17 | — |
| 4-CH$_3$ | 95 (1) | | | | | |
| 3-CH$_3$ | 96 (1) | | | | | |
| 3-CH$_3$O | | 0.41(6H,s),2.94 (2H,s),3.81(3H,s), 6.80-7.45(4H,m) | | | | |
| 3-Cl | | 0.41(6H,s),2.93 (2H,s),7.25-7.77 (4H,m) | | | | |
| 2-C$_2$H$_5$ | | 0.47(6H,s),1.25 (3H,t,J=7Hz),1.76 (2H,q,J=7Hz),3.06, (2H,s),7.02-7.55 (4H,m) | | | | |
| 2-C$_2$H$_5$O | | 0.40(6H,s),1.41 (3H,t,J=7Hz),3.09 (2H,s),4.04(2H,q, J=7Hz),6.75-7.49 (4H,m) | | | | |
| 3-C$_2$H$_5$O | | 0.40(6H,s),1.41 (3H,t,J=7Hz),2.94 (2H,s),4.05(2H,q, J=7Hz),6.82-7.48 (4H,m) | | | | |
| 4-C$_2$H$_5$S | 95 (1) | | C$_{11}$H$_{17}$ClSSi | | | |
| | | | 53.95 | 7.00 | 14.48 | — |

TABLE 3-continued

| $R^{1b}$ | bp°C. (mmHg) | NMR (CDCl₃,δ,ppm) | Molecular Formula Elementary Analysis Calculated Found | | | |
|---|---|---|---|---|---|---|
| | | | C | H | Cl | F |
| 4-(CH₃)₂CHO | 70 (1) | 53.66 | 7.10 | 14.50 | — | |
| 3,4-OCH₂O | 87 (1) | | | | | |

TABLE 4

| $R^{1b}$ | mp°C. | NMR (CDCl₃,δ,ppm) | Molecular Formula Elementary Analysis Calculated Found | | | |
|---|---|---|---|---|---|---|
| | | | C | H | Cl | F |
| 4-C₂H₅O | 36–38 | 0.31(6H,s),1.32 (1H,brs),1.37(3H, t,J=7Hz),3.47(2H, s),3.99(2H,q,J= 7Hz),6.82(2H,d,J= 8Hz),7.38(2H,d,J= 8Hz) | C₁₁H₁₈O₂Si 62.81 62.56 | 8.63 8.77 | — — | — — |
| H | | | C₉H₁₄OSi 65.00 64.92 | 8.49 8.52 | — — | — — |
| 4-Cl | | | C₉H₁₃ClOSi 53.85 53.89 | 6.53 6.65 | 17.66 17.72 | — — |
| 4-F | | | C₉H₁₃FOSi 58.66 58.05 | 7.11 7.63 | — — | 10.31 10.12 |
| 4-CH₃O | | | C₁₀H₁₆O₂Si 61.18 60.30 | 8.22 8.19 | — — | — — |
| 4-CH₃ | | 0.32(6H,s),1.43 (1H,brs),2.33 (3H,s),3.53(2H,s), 7.17(2H,d,J=8Hz), 7.45(2H,d,J=8Hz) | | | | |
| 3-CH₃ | | 0.30(6H,s),1.56 (1H,brs),2.32(3H, s),3.51(2H,s), 7.13–7.40(4H,m) | | | | |
| 3-CH₃O | | | C₁₀H₁₆O₂Si 61.18 60.83 | 8.22 8.26 | — — | — — |
| 3-Cl | | | C₉H₁₃ClOSi 53.85 54.76 | 6.53 6.80 | 17.66 16.52 | — — |
| 2-C₂H₅ | | | C₁₁H₁₈OSi 67.98 67.52 | 9.33 9.26 | — — | — — |
| 2-C₂H₅O | | | C₁₁H₁₈O₂Si 62.81 62.61 | 8.62 8.66 | — — | — — |
| 3-C₂H₅O | | 0.33(6H,s),0.97 (1H,brs),1.40(3H, t,J=7Hz),3.55(2H, s),4.03(2H,q,J= 7Hz),6.75–7.40 (4H,m) | | | | |
| 4-C₂H₅S | | | C₁₁H₁₈OSSi 58.35 58.79 | 8.01 8.02 | — — | — — |
| 4-(CH₃)₂CHO | | 0.32(6H,s),0.94 (1H,brs),1.33(6H, d,J=7Hz),3.53(2H, s),4.56(1H,hept., J=7Hz),6.87(2H,d, J=8Hz),7.43(2H, d,J=8Hz) | | | | |
| 4-CF₂HO | | 0.34(6H,s),1.06 (1H,brs),3.53(2H, s),6.43(1H,t,J= 73Hz),7.03(2H,d, J=8Hz),7.48(2H,d, J=8Hz) | | | | |
| 3,4-OCH₂O | | | C₁₀H₁₄O₃Si 57.11 | 6.66 | — | — |

TABLE 4-continued

| R$^{1b}$ | mp°C. | NMR (CDCl$_3$,δ,ppm) | Molecular Formula Elementary Analysis Calculated Found | | | |
|---|---|---|---|---|---|---|
| | | | C | H | Cl | F |
| | | | 57.16 | 6.66 | — | — |

| Formulation 1 Oil solution | |
|---|---|
| Ingredient | Part by weight |
| Compound (I) of the Invention | 0.5 |
| Kerosene | q.s. |

The active ingredient is dissolved in kerosene to make a total volume of 100 part by weight.

| Formulation 2 Emulsifiable Concentrate | |
|---|---|
| Ingredient | Part by weight |
| Compound (I) of the invention | 10 |
| Solpol 3005X ® (Emulsifing agent) | 10 |
| Xylene | 80 |

The above ingredients are mixed to make emulsion.

| Formulation 3 Dust | |
|---|---|
| Ingredient | Part by weight |
| Compound (I) of the invention | 2 |
| Clay | 88 |
| Talk | 10 |

The above ingredients are uniformly mixed to obtain the dust preparation.

| Formulation 4 Wettable Powder | |
|---|---|
| Ingredient | Part by weight |
| Compound (I) of the invention | 30 |
| Diatomaceous earth | 45 |
| White carbon | 20 |
| Sodium lauryl sulfate | 3 |
| Sodium lignin sulfonate | 2 |

The above ingredients are uniformly admixed to obtain the wettable powder preparation.

TEST 1

Samples

The compound of the invention to be tested is dissolved in a minimum amount of DMF. Distilled water containing Tween 20 at the concentration of 100 ppm is thereto added to prepare a series of samples of the desired concentrations.

Test Procedure

A. Suppression of *Spodoptera litura* larvae

Cabbage leaves (5×5 cm) were immersed in the sample solution as prepared above and air dried. Two leaves were placed in a petri dish (9 cm diameter) and 10 second-instar larvae of *Spodoptera litura* were placed in the dish. The dish was held at 25° C. and the mortality of the larvae was measured after 48 hours.

C. Suppression of *Plutella xylostella* larvae

Cabbage leaf (5×5 cm) was immersed in the sample solution and air dried. The leaf was placed in a petri dish (9 cm diameter) and 10 third-instar larvae of *Plutella xylostella* were placed in the dish. The dish was held at 25° C. and the mortality of the larvae was measured after 48 hours.

D. Suppression of *Adoxophyes* sp. larvae

Whole tea leaves were immersed in the sample solution and air dried. Three leaves were placed in a polyethylene petri dish (6 cm diameter, 4 cm depth) and 10 forth-instar larvae of *Adoxophyes* sp. were placed in the dish. The dish was held at 25° C. and the mortality of the larvae was measured after 48 hours.

F. Suppression of *Nephotettix cincticeps* larvae

Six or seven rice seedlings of 1.5 to 2 plant age in leaf number were bundled and the roots were wrapped in sponge. The seedlings were placed in a polyethylene cup (diameter 6 cm, depth 4 cm) and the cup is placed in a rotary application tower, whereby the vegetative parts of the seedlings were sprayed with 2 ml of the sample solution and air dried. The treated seedlings were covered with a transparent plastic cylinder and ten female larvae were placed in the cylinder. The atmosphere in the cylinder was kept at 25° C., and the mortality after 48 hours was measured.

I. Suppression of *Myzus persicae* larvae

A polyethylene cup (diameter 6 cm, depth 4 cm) was filled with 0.3% agar gel and a piece of Chinese cabbage leaf (3×3 cm) was placed on the gel. A no-wing adult of *Myzus persicae* was placed on the cabbage and allowed to egg-deposit while keeping the surrounding atmosphere at 25° C. for 24 hours. After removing the adult, 2 ml of the sample was sprayed on the leaf under a rotary application tower. The test system was kept at 25° C. for 48 hours and the mortality of born larvae was measured.

M. Suppression of *Tetranychus cinnabrinus*

A polyethylene cup (diameter 6 cm, depth 4 cm) was filled with 0.3% agar gel and a piece of bush bean leaf (diameter 2 cm) was placed on the gel. Twelve adults of *Tetranychus cinnabrinus* were placed on the leaf. After 24 hours at 25° C., dead and feeble worms were removed and 2 ml of the sample solution was sprayed on the leaf under a rotary application tower. Following such treatment the test system was kept at 25° C. and the mortality was measured after 48 hours.

O. Suppression of *Tetranychus urticae*

The same test procedure as above was repeated on *Tetranychus urticae*.

R. Suppression of *Periplaneta americana* larvae

A filter paper soaked with the sample solution was placed in a petri dish (diameter 9 cm). Five *Periplaneta americana* larvae within 7 days after hatching were placed in the dish hold at 25° C. and the mortality after 48 hours was measured.

S. Suppression of *Bruchus pisorum*

Ten *Bruchus pisorum* adults within 24 hours after hatching were placed in a screw cylinder (diameter 1.8 cm, height 5 cm) with stainless nets at the up-and-down openings. The cylinder was submerged in the sample solution, and the worms exposed to the solution were air dried. THe mortality was measured after 48 hours at 25° C.

Test Results

Table 5 shows the test results wherein the mortality (%) of each worm at the concentration of 250 ppm of each of the indicated compounds (I) is given using the following codes:

A: *Spodoptera litura* (larvae)
C: *Plutella xylostella* (larvae)
D: *Adoxophyes sp.* (larvae)
F: *Nephotettix cincticeps* (larvae)
I: *Myzus persicae* (larvae)
M: *Tetranychus cinnabrinus* (adult)
O: *Tetranychus urticae* (adult)
R: *Periplaneta americana* (larvae)
S: *Bruchus pisorum* (adult)

TABLE 5

| Compound No. | A | C | D | F | I | M | O | R | S |
|---|---|---|---|---|---|---|---|---|---|
| 1 | | 80 | | | | | | | |
| 6 | 100 | 100 | 100 | | | | | 100 | 83 |
| 8 | | 90 | 100 | | | | | 100 | 100 |
| 7 | | | 95 | | | | | 100 | 100 |
| 9 | | | 100 | | | | | | |
| 15 | | | 100 | | | | | 100 | 100 |
| 17 | | | 100 | | | | | 100 | 77 |
| 33 | | 100 | 80 | | | | | | |
| 25 | | 90 | 90 | | | | | | 100 |
| 39 | 90 | 90 | 95 | 100 | | | | 100 | |
| 41 | 100 | 100 | 95 | | 85 | 83 | | 100 | |
| 42 | | 90 | | | 97 | | | 100 | |
| 43 | 100 | 80 | 90 | | 100 | 94 | 97 | 100 | |
| 28 | | 80 | | | | | | | |
| 27 | 100 | 70 | 100 | 87 | 83 | | | | |
| 44 | | 100 | 80 | | | 93 | 69 | 100 | |
| 29 | 75 | 85 | 70 | | 88 | | | 100 | |
| 40 | | | | | | | 97 | 86 | 100 |

TEST 2

This test was conducted using *Oryzias latipes* (female adult) (whole length 2.74±0.089 cm, length without tail 2.25±0.069 cm, weight 0.199±0.0176 g) according to the method described in Japanese Industrial Standard K-0102(1). No feed was given to the fish for 48 hours before test. Compound No. 1 and No. 27 were dissolved in aqueous DMSO solution at a given concentration in a glass beaker (3 L). Ten fish were kept in the beaker at 25.0±0.5° C. The mortality was measured at one hour interval until 8 hours after treatment, and then 24 hours intervals (total 96 hours). Table 6 lists the test results.

TABLE 6

| Treatment | Concentration (mg/l) | Mortality 24 | 48 | 72 | 96 (hours) |
|---|---|---|---|---|---|
| Compound No. 1 | 100 | 0 | 0 | 0 | 0 |
| Compound No. 27 | 100 | 0 | 0 | 0 | 0 |
| | 56.2 | 0 | 0 | 0 | 0 |
| | 31.0 | 0 | 0 | 0 | 0 |

What we claim is:

1. A compound of the formula:

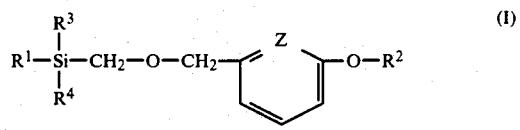

wherein $R^1$ and $R^2$ are each phenyl optionally substituted by one selected from the group consisting of $C_1$-$C_5$ alkyl, $C_1$-$C_5$ alkoxy, $C_1$-$C_5$ alkylthio, $C_1$-$C_5$ alkylenedioxy, halogen, nitro, and halogeno-$C_1$-$C_5$ alkoxy; $R^3$ and $R^4$ are each $C_1$-$C_5$ alkyl; and Z is N or CH.

2. A compound according to claim 1 wherein $R^2$ is phenyl substituted by one selected from the group consisting of $C_1$-$C_5$ alkyl, $C_1$-$C_5$ alkoxy, $C_1$-$C_5$ alkylthio, $C_1$-$C_5$ alkylenedioxy, halogen, nitro, and halogeno-$C_1$-$C_5$ alkoxy and, $R^1$, $R^3$, $R^4$ and Z are as defined in claim 1.

3. A compound according to claim 1 wherein $R^1$ is $C_1$-$C_5$ alkylthiophenyl, $C_1$-$C_5$ alkylenedioxyphenyl, nitrophenyl or halogeno-$C_1$-$C_5$ alkoxyphenyl, $R^2$ is phenyl, $R^3$, $R^4$ and Z are as defined in claim 1.

4. A compound according to claim 3 wherein $R^3$ and $R^4$ are each $C_2$-$C_5$ alkyl.

5. A pesticidal composition comprising as an active ingredient from 0.1 to 95% by weight of a compound of the formula (I) as defined in claim 1 associated with at least one carrier or diluent therefor.

6. A method of suppressing pests which comprises applying to the locus of the pests a compound of the formula (I) as defined in claim 1.

7. A process for preparing a compound of the formula (I) as defined in claim 1 which comprises reacting a compound of the formula:

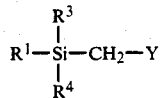

wherein Y is hydroxyl or its metal salt and $R^1$, $R^3$, and $R^4$ are as defined above with a compound of the formula:

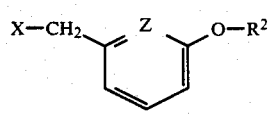

wherein X is halogen, and $R^2$ and Z are as defined above.

* * * * *